United States Patent [19]
Bennett et al.

[11] Patent Number: 5,226,413
[45] Date of Patent: Jul. 13, 1993

[54] RATE RESPONSIVE PACEMAKER AND METHOD FOR AUTOMATICALLY INITIALIZING THE SAME

[75] Inventors: Tommy D. Bennett, Shoreview; Lucy M. Nichols, Maple Grove; Glenn M. Roline, Anoka; David L. Thompson, Fridley, all of Minn.

[73] Assignee: Medtronic, Inc., Minneapolis, Minn.

[21] Appl. No.: 567,372

[22] Filed: Aug. 14, 1990

[51] Int. Cl.⁵ ............................................. A61N 1/362
[52] U.S. Cl. ............................................. 128/419 PG
[58] Field of Search ............................ 128/419 PG

[56] References Cited

U.S. PATENT DOCUMENTS

| | | | |
|---|---|---|---|
| 4,485,813 | 12/1984 | Anderson et al. | 128/675 |
| 4,719,920 | 1/1988 | Alt et al. | 128/419 |
| 4,867,162 | 9/1989 | Schaldach | 128/419 |
| 4,901,726 | 2/1990 | Hansen | 128/419 |

OTHER PUBLICATIONS

Clinical Experience with a New Activity Sensing Rate Modulated Pacemaker Using Autoprogrammability. by V. Mahaux, et al., in PACE vol. 12, Aug. 19, 1989 issue, pp. 1362 through 1368.

*Primary Examiner*—Kyle L. Howell
*Assistant Examiner*—Scott M. Getzow
*Attorney, Agent, or Firm*—Harold R. Patton; Gregory P. Gadson

[57] ABSTRACT

A pacemaker system includes a dual sensor implantable pacemaker and an external programmer for automatically and simultaneously optimizing and initializing a plurality of pacing parameters. The pacemaker includes means for automatically initializing a sensitivity threshold, pacing pulse width, pacing pulse amplitude, activity threshold, and pressure rate response gain setting.

14 Claims, 10 Drawing Sheets

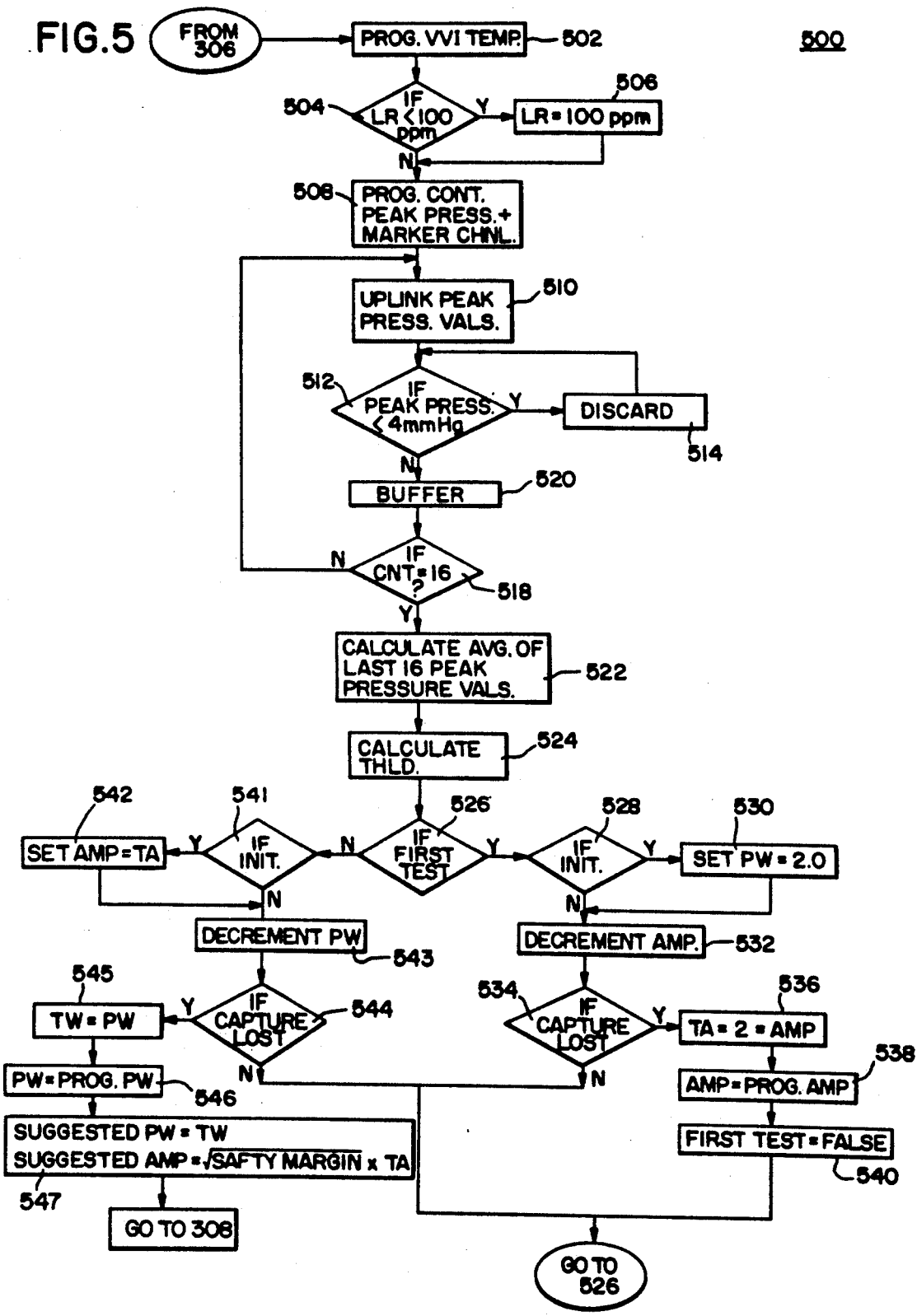

RATE RESPONSIVE PACEMAKER AND METHOD FOR AUTOMATICALLY INITIALIZING THE SAME

BACKGROUND OF THE INVENTION

1. Field of the Invention

The present invention generally relates to medical cardiac pacers, and more particularly, it pertains to a method for initializing a cardiac pacemakers of the type which responds to the patient's metabolic demand and varies the pacing rate in accordance therewith.

2. Description of the Prior Art

Early cardiac pacemakers provided a fixed-rate stimulation pulse generator that could be reset, on demand, by sensed atrial and/or ventricular depolarizations. Modern pacemakers include complex stimulation pulse generators, sense amplifiers and leads which can be configured or programmed to operate in single or dual chamber modes of operation, delivering pacing stimuli to the atrium and/or ventricle at fixed rates or rates that vary between an upper rate limit and a lower rate limit.

In recent years, single and dual chamber pacemakers have been developed which measure parameters which are directly or indirectly related to metabolic requirements (e.g., demand for oxygenated blood) and vary the pacing rate in response to such parameters. Such measured parameters include, for example, physical activity of the body, right ventricular blood pressure and the change of right ventricular blood pressure over time, venous blood temperature, venous blood oxygen saturation, respiration, minute ventilation, and various pre and post-systolic time intervals measured by impedance or pressure sensing within the right ventricle of the heart. Such sensor-driven pacemakers have been developed for the purpose of restoring rate response to exercise in patients lacking the ability to increase rate adequately by exertion.

In general, a rate responsive pacemaker includes a sensor which produces an output that varies between a maximum sensor output level and a minimum sensor output level ("Sensor Output"), and a pacing rate is provided by the pacemaker ("Pacing Rate") which typically varies as a linear or monotonic function ("f") of the sensor output, between a selectable lower pacing rate ("Lower Rate") and upper pacing rate ("Upper Rate"). Function f has a selectable slope (i.e. Pacing Rate change/Sensor Output change) adjustable by means of an external programmer in conjunction with the Lower and Upper Rates. Thus, the Pacing Rate typically provided is equal to the pre-selected Lower Rate plus an increment which is a function of the measured Sensor Output, as follows:

Pacing Rate = Lower Rate + f(Sensor Output).

In an effort to minimize patient problems and to prolong or extend the useful life of an implanted pacemaker, it has become common practice in recent years to provide programmable parameters in order to permit the physician to select and adjust the desired parameters to match or optimize the pacing system to the heart's physiologic requirements. The physician may adjust the output energy settings to maximize the pacemaker battery longevity while ensuring an adequate patient safety margin. Additionally, the physician may adjust the sensing threshold to ensure adequate sensing of the intrinsic depolarization of cardiac tissue, while preventing oversensing of unwanted events such as myopotential interference or electromagnetic interference (EMI).

Recently, rate responsive pacing systems with many programmable variables have been developed and marketed. These systems are based upon utilizing a sensor derived variable that is an indicator of the patient's true metabolic and physiologic needs. Similarly, programmable parameters are required to enable and to optimize this rate response function.

Historically, the above parameters have been manually programmed and adjusted or optimized in an ad hoc iterative process. Often because the process is difficult and lengthy, patient parameters are not optimized, but left at nominal, shipping parameters.

Wherefore, it is desirable to design a pacemaker system and a method of programming the same for automatically initializing the optimal parameter settings either at the time of implant, or thereafter during subsequent follow-ups, with minimal guess or estimation on the part of the physician. The desired pacemaker system should more accurately determine the programmable parameter values and reduce the time required to implant or conduct follow-up sessions.

One attempt at optimizing pacing parameters is described in U.S. Pat. No. 4,867,162 issued to Schaldach. The Schaldach patent generally discloses a cardiac pacer having digital logic circuitry for choosing the characteristics of the pulses to be generated in responses to signals from several physiologic sensors detecting different exercise-related body functions.

The Schaldach pacer uses an external variable for determining the physiological exertion. This external variable is not detectable in the normal operation, but is ascertainable indirectly during the pacing operation from other physiological measured variables. Look-up tables are then used to associate the external variables to the physiological variables.

While this teaching constitutes an improvement over the conventional methods, it has not proven to be completely satisfactory in addressing and resolving the optimization problems associated with the optimization process.

The initialization process disclosed in the Schladach patent is lengthy and somewhat complicated. It generally requires high rate pacing and a substantial memory size for processing the information. Furthermore, the accuracy of the initialization might be compromised due to the extrapolation of the derived data.

Another attempt for automatically adjusting the settings is described in: "Clinical Experience with a New Activity Sensing Rate Modulated Pacemaker Using Autoprogrammability" by V. Mahaux et al., in PACE volume 12, August 1989 issue, pages 1362 through 1368. This article describes the autoprogrammability feature used in the Siemens, Elema AB's Sensolog 703 pacemaker.

The Sensolog 703 pacemaker is a single chamber activity sensing, rate modulated, multiprogrammable pulse generator whose main programmable variables include pacing mode, sensor states, minimum and maximum rates, recovery time and responsiveness. The responsiveness of the pulse generator is determined by two calibration points corresponding to two levels of exercise called "low work" (LW) and "high work" (HW). During the adjustment procedure, the physician defines the desired pacing rates for LW and HW, and asks the patient to perform the corresponding physical activities every thirty seconds. The last sensor output registered at each level of activity is compared to the desired pacing rate by an algorithm in the programmer and optimal sets of slope and threshold values are suggested to the clinician which he may use or not. The Senslog 703 pacemaker needs to be manually reprogrammed at various phases after implant, and various tables relating settings to corresponding slope-threshold combinations as well as tables relating rate response to sensor values are also required for programming the parameters.

It is therefore obvious that the Sensolog 703 pacemaker has not demonstrated the ease of use required for an optimal operation of the pacemaker. In fact, the physician's personal interaction is still necessitated at various phases of the automation process. Furthermore, the multi-phase automatization somewhat defeats the object behind the simplification of the operation of the pulse generator, and does not alleviate many of the problems associated with conventional programming methods.

Additionally, the proposed automization method has not attained, nor does it inspire the level of confidence expected from an automized procedure.

Similarly, other pacemakers, such as Medtronic Inc.'s Activitrax II Models 8412-14, Medtronic, Inc.'s Legend Models 8416-18, Cook Pacemaker Corporation's Sensor Model Kelvin 500, Telectronics' Meta MV Model 1202, Cordis Pacing Systems' Prism CL Model 450A, and Intermedics, Inc.'s Nova MR pacemakers have incorporated the programmability feature of various variables. However, these pacemakers generally require manual programming for entering the values of the desired parameters, in that the operating physicians estimate, through successive trials, the approximate settings for these parameters.

Medtronic Inc.'s Legend and Activitrax II are single chamber, multi-programmable, rate responsive pacemakers, whose rate responds to physical activity. These pacemakers may be programmed to the following parameters: mode, sensitivity, refractory period, pulse amplitude, pulse width, lower and upper rates and rate response gain and activity threshold.

Cook Pacemaker Corporation's Sensor Model Kelvin 500 is a unipolar, multimodal, rate responsive, processor-based pacemaker capable of monitoring the temperature of the blood in the right heart, and making the decision to increase the rate as a result of the patient's physiologic stress. This pacemaker allows for the manual programming of the following parameters: Mode, sensitivity, refractory period, pulse width, lower and upper rates, and interim rate.

Teletronics' Meta MV Model 1202 is an implantable multi-programmable bipolar cardiac pulse generator with telemetry. It can be programmed to operate in one of four pacing modes; demand inhibited (VVI or AAI); asynchronous (VOO or AOO); demand inhibited with an automatic rate response based on sensed changes in respiratory minute ventilation; or adaptive non-rate responsive mode. The following operating parameters are also programmable: Standby rate; sensitivity; pulse amplitude; pulse width; refractory period; minimum heart rate; and maximum heart rate.

Cordis Pacing Systems' Prism CL Model 450A is a rate responsive single-chamber, multi-programmable, implantable pulse generator with telemetry, for pacing and sensing in the ventricle. The following parameters are programmable: pacing modes (VVI, VVT, VOO); rate response (ON, OFF); electrode polarity; minimum and maximum rates; output current; pulse width; sensitivity; refractory period; and automatic calibration.

The pacer functions described in the Cordis pacemaker manual, are as follows: The target Rate Control Parameter (RCP) is the reference RCP that the pacer uses to control the pacing rate. The pacer determines what the appropriate rate should be by comparing the measured RCP to the target RCP. If the measured RCP is different from the target RCP, rate is increased or decreased until the measured RCP equals the target RCP. The target RCP is a dynamic variable which is first determined by an initialization process, which is automatically activated when rate response is programmed ON. The pacer then continuously makes automatic adjustments to the target RCP to adjust rate response.

The initial RCP is determined while the patient is at rest. During initialization, the RCP is measured for approximately 20 paced cycles to establish the target RCP. If intrinsic activity is sensed during the initialization process, initialization is temporarily suspended and the rate is increased by 2.5 ppm every cycle until pacing resumes. Once initialization is completed and the initial target RCP has been established, rate response is automatically initiated and the automatic calibration function is enabled. The pacer indicates the end of the initialization process by issuing an ECG signature in the succeeding cycle.

The automatic calibration feature is described in the pacemaker manual as follows: When rate response is ON, the pacer continuously calibrates the target RCP while making adjustments for drifts in RCP that can occur because of lead maturation, drug therapy, and physiologic factors other than those related to physiologic stresses. The frequency of adjustment depends, in part, on the speed at which calibration occurs (Slow, Medium, or Fast).

Intermedics, Inc.'s Nova MR is an implantable, unipolar pulse generator designed to provide metabolic response pacing to either the atrium or ventricle. It senses variations in blood temperature and uses this information to vary the pacing rate in response to the patient's metabolic demand. The following functions are programmable to determine the pulse generator's response to variations in blood temperature: Rate response; onset detection sensitivity'; and post-exercise rate decay.

It is therefore abundantly clear that while some of these pacemakers have accomplished satisfactory results, they have not taught a method for simultaneously and automatically initializing optimal parameter settings for sensitivity threshold; pulse amplitude and width; activity threshold; and pressure (dP/dt) rate response gain, either at the time of implant, or thereafter, during subsequent follow-ups, with minimal guess or estimation on the part of the physician.

BRIEF SUMMARY OF THE INVENTION

It is therefore one object of the present invention to address the above problems and to provide adequate solutions thereto.

Briefly, the above and further objects and features of the present invention are realized by providing a pacemaker system and method for automatically and simultaneously optimizing and initializing a plurality of pacing parameters. The pacemaker system includes a dual sensor implantable pacemaker and an external programmer. The pacemaker includes means for automatically initializing the sensitivity threshold, pacing pulse width, pacing pulse amplitude, activity threshold, and pressure rate response gain setting.

The process of automatically initializing the sensitivity threshold includes the steps of calculating, on a periodic basis, a sense ratio factor (SRF) according to the following equation:

$$SRF = \frac{(\text{Peak Sense})}{(\text{Sense Threshold}) \times (\text{Recommended Safety Margin})}$$

where the Recommended Safety Margin is calculated as follows:

$$\text{Recommended Safety Margin} = \frac{(\% \text{ Safety Margin} + P\%)}{100}$$

and the Safety Margin is a programmable value.

The recommended Sensitivity threshold is then determined according to the following equation:
Recommended Sensitivity
Threshold = SRF × Programmed Threshold.

The process of automatically initializing the pacing pulse width and amplitude parameters includes the steps of measuring the peak pressure values, and averaging the valid peak pressure values over a predetermined interval of time to monitor for loss of capture. A rheobase point is determined along a strength duration curve, and a chronaxie point is determined based on the coordinates of the rheobase.

The pulse width and amplitude parameters are then determined according to the following equations:

Recommended Pulse Width = Pulse Width of the Chronaxie.

Recommended Pulse Amplitude = k × the Pulse Amplitude of Chronaxie, where "k" is a programmable coefficient.

The process of automatically initializing an activity threshold parameter includes the steps of setting the activity threshold to an initial value, and periodically counting the sensed activity events at rest. Thereafter, one of a plurality of higher settings for the activity threshold is automatically selected if the counter indicates a positve activity count, and one of a plurality of lower settings for said activity threshold is then automatically selected if the counter indicates a zero activity count.

The process of automatically initializing a pressure rate response gain setting position with regard to the resting dP/dt and resting rate including the steps of counting and measuring valid peak pressure values (dP/dt) and average rate. The peak pressure and rate values are averaged over a predetermined interval of time, and the resting dP/dt value is extrapolated to 70 ppm according to the following equation:

$$\text{Resting } dP/dt = \frac{[70 \text{ ppm} \times \text{Average Peak } dP/dt]}{\text{Average Resting Rate}}$$

Thereafter, the resting dP/dt value is used to set the rate response gain as follows:

$$\text{Rate Response Gain} = \frac{\text{Upper Rate} - \text{Resting Rate}}{\text{Resting } dP/dt}$$

BRIEF DESCRIPTION OF THE DRAWINGS

The above and other objects and features of the present invention and the manner of attaining them, will become apparent, and the invention itself will be best understood, by reference to the following description and the accompanying drawings, wherein:

FIG. 5 a simplified flow chart illustrating an automatic initialization routine for selecting the optimal pulse width and amplitude parameters according to the present invention;

DESCRIPTION OF THE PREFERRED EMBODIMENT

Figure 1:
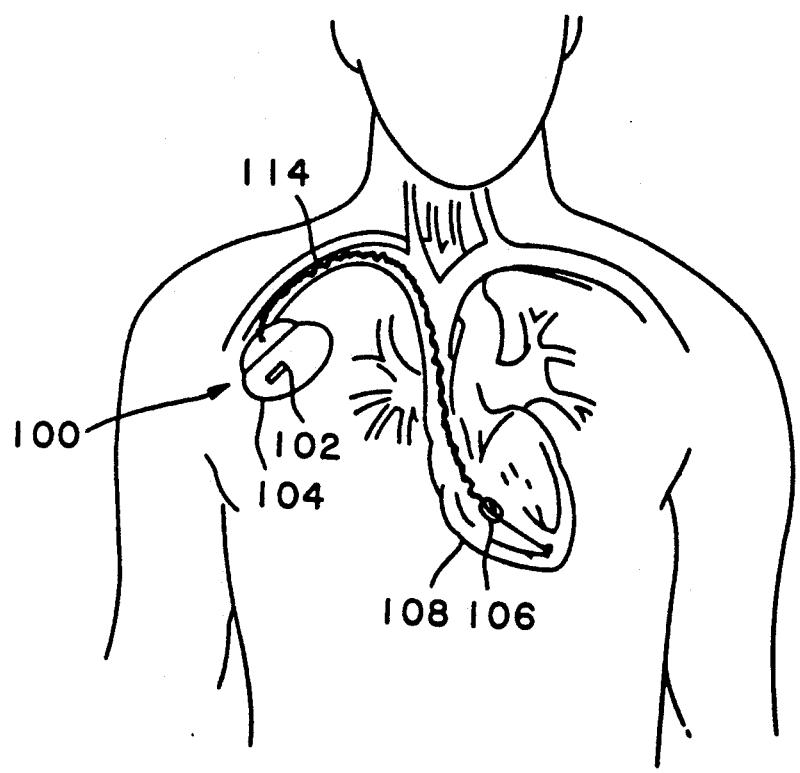
FIG. 1 graphically illustrates a pacemaker employing the present invention.

Referring now to the drawings and more particularly to FIG. 1 thereof, there is illustrated a multi-sensor pacemaker 100 according to the present invention. Although the present invention is described in conjunction with a microprocessor based architecture, it should be understood that the invention can also be practiced in digital logic-base, custom integrated circuit architecture.

The preferred embodiment of the pacemaker 100 includes two sensors, namely, an activity sensor 102, and a pressure sensor 106, each of which provides a sensor output which varies as a function of a measured parameter that relates to the patient's activity level and metabolic requirements. Since each sensor output can be utilized by the pacemaker 100 to control the pacing rate, each sensor output is referred to as a rate-control parameter (RCP).

In the preferred embodiment, the activity sensor 102 includes a piezoelectric motion detector secured to a can or housing 104, and provides an output that is proportional to the patient's physical activity. The pressure sensor 106 is implanted within the patient's heart 108, and includes a dynamic pressure transducer incorporated within a pacing lead 114, which, in turn, is coupled to a pulse generator housed within the can 104. The pacemaker 100 can, additionally, use the output from the dynamic pressure sensor 106 to monitor the mechanical activity of the heart 108, which will allow the pacemaker 100 to monitor stimulation thresholds and to automatically adjust the pacing output parameters.

The operation of the sensors 102 and 106 is described in greater details in the co-pending U.S. patent applications entitled "OPTIMIZATION FOR RATE RESPONSIVE CARDIAC PACEMAKER", Ser. No. 567,476, and "RATE RESPONSIVE PACEMAKER AND METHODS FOR OPTIMIZING ITS OPERATION", Ser. No. 567,882, both are held by the same assignee as the present invention, are filed on even date herewith, and are incorporated herein by reference. It should be, however, understood that the present invention is not limited to a dual sensor pacemaker, and that other sensors beside pressure and activity sensors could also be used according to the present invention.

The activity sensor 102 is disclosed in U.S. Pat. No. 4,428,378 issued to Anderson et al., entitled "RATE ADAPTIVE PACER", which is held by the same assignee as the present invention and which is incorporated herein by reference. This activity sensor measures a rate-control parameter related to physiologic forces associated with body activity ($RCP_{act}$), and provides an output which is proportional to the patient's activity.

The second sensor is a dynamic pressure sensor, such as the type disclosed in U.S. Pat. No. 4,485,813 issued to Anderson et al., entitled "IMPLANTABLE DYNAMIC PRESSURE TRANSDUCER SYSTEM", which is held by the same assignee as the present invention and which is incorporated herein by reference. The pressure sensor 106 measures a rate-control parameter related to changes in fluid pressure associated with the heart's mechanical activity or contractions ($RCP_{press}$), and provides an output which is proportional to the magnitude of the change in fluid pressure in the patient's heart. In the preferred embodiment, the pressure sensor 106 comprises a time derivative of the fluid pressure applied to the pressure sensor 106 within the right ventricle of the patient's heart (i.e., dP/dt).

Figure 2:
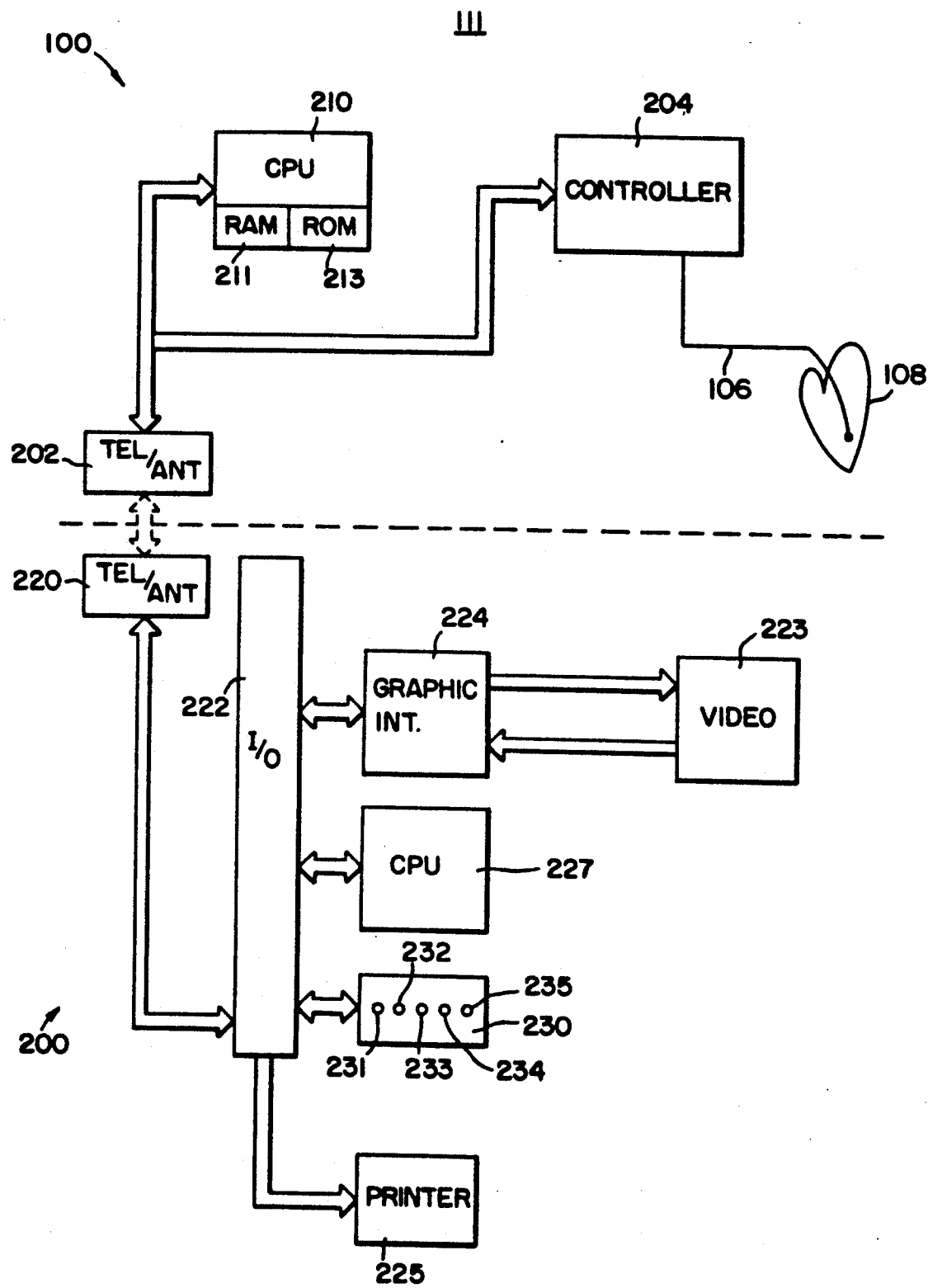
FIG. 2 is a system block diagram of a pacemaker system illustrating the pacemaker of FIG. 1 in use with a programmer according to the present invention.

FIG. 2 is a simplified system block diagram of a pacemaker system 111 and illustrates the pacemaker 100, in use with a programmer 200 according to the present invention. The programmer 200 uses a software program which allows the physician, among other applications, to reprogram or interrogate the pacemaker 100, and to cause the pacemaker 100 to uplink, via telemetry, measured values or logged data values to the programmer 200.

The hardware structure of the pacemaker system 111, i.e., the pacemaker 100 and the programmer 200 will now be described. The pacemaker 100 communicates with the programmer 200 over a telemetry port and antenna 202, and generally comprises a conventional multi-programmable system or controller 204. The multi-programmable system 204 contains conventional pacing and sensing functions known in the art.

A steroid-tipped, unipolar lead 206 with a pressure transducer interfaces between the multi-programmable system 204 and the heart 108.

The central processing unit (CPU) 210 includes random-access memory (RAM) 211 and read-only memory (ROM) 213 and manages desired function and stores temporary and programmed variables.

It should be noted that signal processing between the pacemaker 100 and the programmer 200 is accomplished in the manner described below in connection with FIGS. 3 through 7, and memories and data linkages are generated by suitable programming or software located in the programmer 200 memory or the memory of the pacemaker CPU 210.

Data transfer between the antenna/telemetry port 202 and the programmer 200 is effected via a programmer antenna/telemetry head 220, which, in turn, communicates with the corresponding telemetry input/output (I/O) unit 222. The I/O unit 222 also interfaces with peripheral output equipment, such as a printer 225, and a video monitor 223 via a graphic display interface 224. The programmer 200 includes its own central processing unit (CPU) 227 which interfaces with the I/O unit 222.

The physician can, by means of the graphic display, view the data uplinked by the pacemaker 100 to the programmer 200, as well as the data to be downlinked to the pacemaker 100. The physician can enter or program the desired data or parameters using conventional means such as a keyboard, a light wand or other similarly available devices.

However, for simplicity purposes, the programmer 200 is described herein as having a control panel 230 with a series of control keys 231, 232, 233, 234 and 235. Other control and function keys are also available for various features, but are not shown in the drawings.

DEFINITIONS

The following definition of terms used herein will assist in a better understanding of the present invention:

Activity Count—A measure of the output of the activity sensor over a predetermined interval of time. In the preferred embodiment, each event in which the amplitude of the output exceeds a predetermined Activity Threshold for a two-second period is counted and retained. The Activity Count is updated every two-second cycle, and its aggregate value comprising the count value accumulated at the end of 3 two-second cycles (i.e., after 6 seconds) is used to calculate the sensor Target Rate for activity.

Activity Rate Response Gain—A setting which corresponds to the slope of the function correlating the activity-based sensor Target Rate to the Activity Count value which corresponds to the activity sensor output. The setting for Activity Rate Response Gain, sometimes alternately referred to as the "activity sensor gain", corresponds to a particular rate response curve (RR). With rate response, the allowed programmable values for the Activity Rate Response Gain range from 1 to 10 at setting intervals of 1.

Activity Threshold—A minimum value which the amplitude of the activity sensor output must exceed to serve as input to the rate determination algorithm. The higher the threshold, the greater the amplitude necessary to become an event counted in the Activity Count. With rate response, the allowed programmable values for the Activity Threshold range from LOW, MEDIUM LOW, MEDIUM, MEDIUM HIGH, and HIGH.

Lower Rate (LR)—A value supplied by the clinician which establishes a lower boundary on the pacing rate. If the sensor is disabled, or its sensor output is not large enough to increase rate, the lower rate is the stimulus rate. With rate response, the allowed programmable values for LR range from 40 ppm to 100 ppm at 1 ppm intervals.

Pacing Rate—The rate calculated by the pacemaker 100 in conjunction with the activity sensor based upon its respective Target Rate and the contribution thereto based upon its respective acceleration and deceleration function.

Pulse Amplitude—Amplitude in volts or amperes of the stimulus pacing pulse.

Pulse Width—Width in milliseconds of the stimulus pacing pulse.

Resting Rate—A rate identified by the clinician during initialization for later use in the pressure-based pacing mode comprising the arithmetic mean of paced or intrinsic rates measured over a predefined time interval with the patient at rest. In the preferred embodiment, the allowed programmable values for the Resting Rate range from 40 ppm to 100 ppm at 5 ppm intervals.

Safety Margin—Value supplied by the physician which specifies the ratio between the amplitude or width of a stimulus which just fails to capture and the desired amplitude or pulse width.

Sense Ratio Factor (SRF)—A ratio of a sensed signal level over the programmed threshold value.

Sensitivity—Value of the sensing amplifier threshold setting.

Target Rate—The rate calculated by the pacemaker 100 in conjunction with the activity or pressure sensors based upon programmed settings and the respective sensor output.

Upper Rate (UR)—A value supplied by the clinician which limits the maximum stimulation rate when the rate responsive mode for activity, is in effect, such that the sensor-driven pacing rate generated by pacemaker 100 does not become hemodynamically excessive. With rate response, the allowed programmable values range from 100 ppm to 175 ppm at 5 ppm intervals, provided UR must also be at least 20 ppm greater than Lower Rate (LR) and Resting Rate.

The general operation of the pacemaker 100 and the programmer 200 will now be described in relation to the pacemaker system 111 of FIG. 2, and the program 300 of FIG. 3. The physician starts the initialization process of the pacemaker 100 by placing the programmer antenna/telemetry head 220 over the implant site of the pacemaker 100 in direct relation with the pacemaker antenna/telemetry port 202, for optimum data communication between the pacemaker 100 and the programmer 200, as indicated by block 301.

The physician has five options to initialize any or all of the following parameters: sensitivity threshold; pulse amplitude and width; activity threshold; and pressure (dP/dt) rate response gain. Each one of the control keys 231, 232, 233, 234 and 235 corresponds to an initialization function setting a flag to "true" as follows: Control key 231 corresponds to sensitivity threshold initialization; control key 232 corresponds to pulse amplitude and width initialization; control key 233 corresponds to activity threshold initialization; control key 234 corresponds to pressure initialization; and control key 235 corresponds to the initialization of all these above five parameters.

It should however be understood to those skilled in the art, after reviewing the present disclosure that other parameters, such as the refractory periods and rate response gain, can also be automatically initialized in a similar manner. The above five parameters have been selected as an example of the present automatic initialization feature. However, there is no intention to limit the present disclosure to these parameters.

Once the physician determines which parameters or parameters he or she wishes to initialize, then the physician presses the corresponding control key. If for instance, the physician wishes to have all the parameters initialized, he or she presses control key 235. In the alternative, control key 233 could be pressed for initializing the activity threshold parameter.

Figure 3:
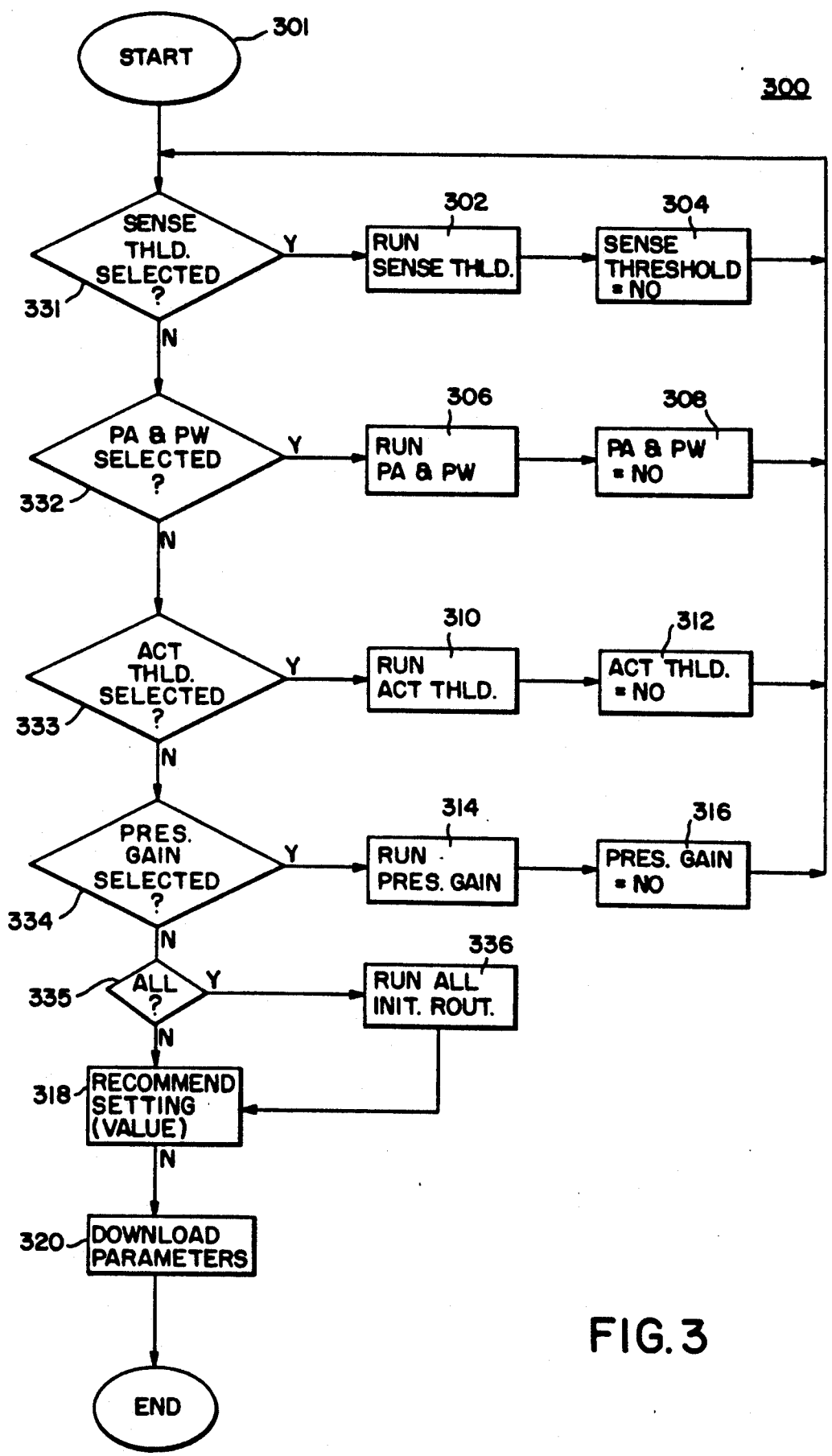
FIG. 3 is a flow chart illustrating the general method for initializing the pacemaker system of FIG. 2.

Turning now to FIG. 3, the software determines, at block 331, whether the operator or physician desires to have the sensitivity threshold parameter initialized. If it has, then, as indicated by block 302, the software runs the automatic initialization routine 400, which will be described later in greater details in connection with FIG. 4. Thereafter, the software program sets a "Sensitivity Threshold=False" flag, at 304, and the software once again inquires whether any other parameter needs to be automatically initialized.

If at block 331, the software determines that the sensitivity threshold parameter has not been selected, then the software inquires at 332, whether the pulse amplitude/width parameters have been selected for initialization. If they have, then, as indicated by block 306, the software runs the automatic initialization routine 500, which will be described later in greater details in connection with FIG. 5. Thereafter, the software program sets a "Pulse Amplitude/Width=False" flag, at 308, and the software once again inquires whether any other parameter needs to be automatically initialized.

If at block 332, the software determines that the pulse width and amplitude parameters have not been selected, then the software inquires at 333, whether the activity threshold parameter has been selected for initialization. If it has, then, as indicated by block 310, the software runs the automatic initialization routine 600, which will be described later in greater details in connection with FIG. 6. Thereafter, the software program sets an "Activity Threshold=False" flag, at 312, and the software once again inquires whether any other parameter needs to be automatically initialized.

If at block 333, the software determines that the activity threshold parameter has not been selected, then the software inquires at 334, whether the pressure gain parameter has been selected for initialization. If it has, then, as indicated by block 314, the software runs the automatic initialization routine 700, which will be described later in greater details in connection with FIG. 7. Thereafter, the software program sets a "Pressure Gain=False" flag, at 316, and the software once again inquires whether any other parameter needs to be automatically initialized.

If at block 335, the software determined that all the parameters have been selected, then the software runs all the initialization routines 400, 500, 600 and 700 and then recommends the preferred settings at 318.

If no other parameters have been selected for initialization, then, as indicated at 318, the initialized parameters are displayed on the monitor 223 as recommended optimal values. If the physician approves of such recommended values, then as indicated at 320, he or she simply presses a "Program" key (not shown), and the recommended values are downlinked to the pacemaker 100. In the alternative, the physician might selectively downlink the parameters he or she approves of, and reprogram or modify the remaining parameters in accordance with conventional practices.

While the preferred embodiment provides for the physician's precautionary check, it should be understood that the recommended parameters could, in the alternative, be downloaded without the physician's intervention.

Figure 4:
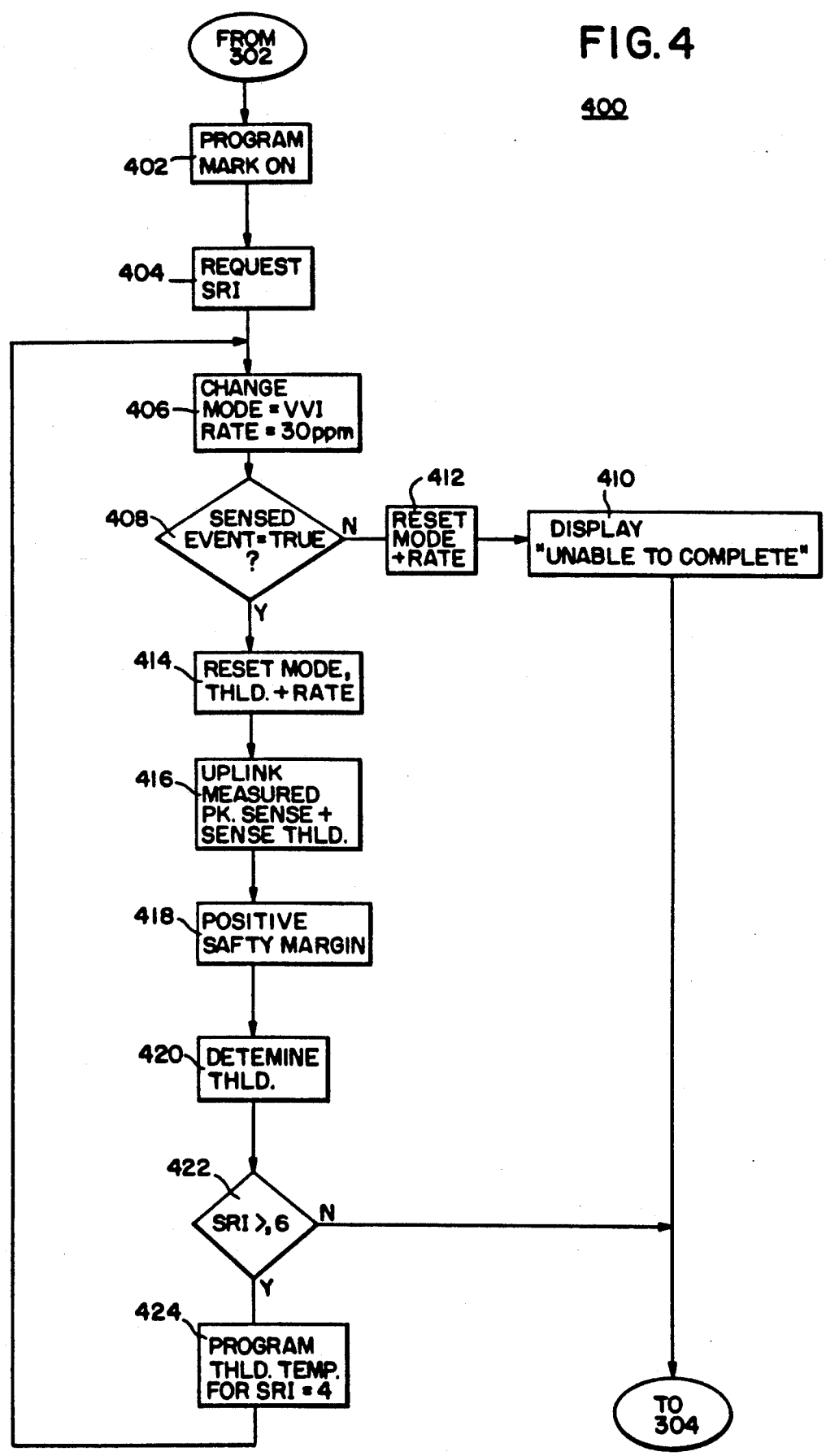
FIG. 4 is a simplified flow chart illustrating an automatic initialization routine for selecting the optimal sensitivity threshold according to the present invention.

Turning now to FIG. 4 of the drawings, there is illustrated, in a simplified flow chart format, the automatic initialization routine 400 for selecting the optimal sensitivity threshold. The purpose of this automatic initialization is to rapidly and accurately set the sense amplifier (not shown) threshold setting and to allow for an adequate margin of safety, in order to ensure that it is neither oversensing nor undersensing.

The software starts by enabling a marker channel at 402. As defined herein, the marker channel refers to a family of event-identifying codes which are telemetered to the programmer 200 to indicate the occurrence of specific events, such as sensed and paced events, in the pacemaker 100. A marker channel telemetry system is described in detail in U.S. Pat. No. 4,374,382, entitled "MARKER CHANNEL TELEMETRY SYSTEM FOR A MEDICAL DEVICE", issued to Markowitz, and assigned to the Medtronic, Inc. This patent is incorporated herein by reference. In a default transmission mode, or upon receiving the proper programming message, the pacemaker 100 transmits a marker code indicating the occurrence of sensing and pacing events in the heart. The marker channel includes a continuous transmission of idle frames until the event to be marked occurs.

Figure 4A:
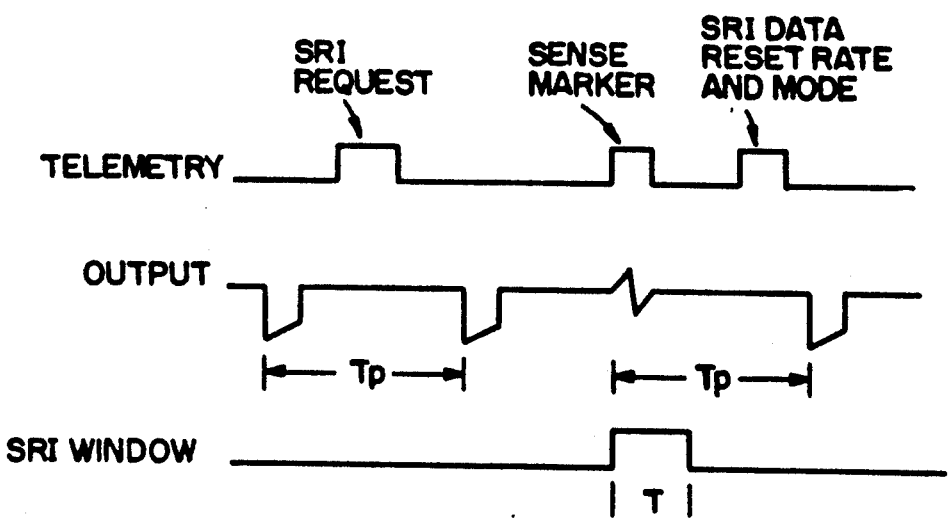
FIG. 4A is a timing diagram used in the automatic initialization routine of FIG. 4.

As indicated at 404, the software automatically requests the Sense Ratio Factor (SRF) feature, whereby the software calculates, on a cycle-by-cycle basis or once upon request, a ratio of signal level over the programmed threshold following the sense-amplifier detection. FIG. 4A is a timing diagram illustrating the SRF request and the SRF window "T", with respect to the pacemaker output and the programmed interval "$T_p$".

The SRF is calculated as follows:

$$SRF = \frac{(Peak\ Sense)}{(Sense\ Threshold) \times (Recommended\ Safety\ Margin)}$$

where the Recommended Safety Margin =

$$\frac{[(\%\ Safety\ Margin + 100\%)]}{100}$$

The software then automatically, temporarily switches the operating mode of the pacemaker 100 to VVI mode and sets the pacing rate to the lowest allowable rate, such as 30 pulse per minute (ppm). In this setting the pacemaker 100 is in a demand mode and the low pacing rate permits capture of a sensed event from an intrinsic depolarization.

Next, the software determines at 408, whether an event has been sensed during the 30 ppm escape interval. If it has not, then the pacing rate, the pacing mode and the sensitivity threshold are reset, at 412, to their original or programmed settings, prior to the initialization process, to ensure the safety of the patient. As shown in FIG. 4 at 410, the following message is displayed on the monitor 223, "Unable to Complete", indicating that the programmer 200 is unable to recommend a sensitivity threshold, and the physician has the option to either rerun the initialization routine at a later time, or to set the sensitivity threshold according to previous conventional practices.

Figure 4B:
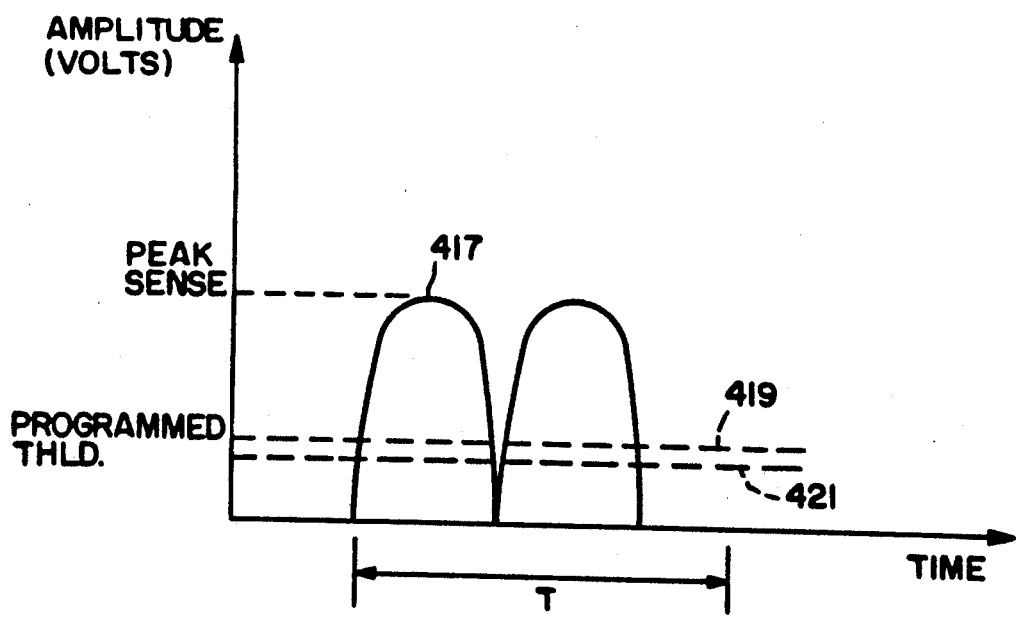
FIG. 4B is a graph showing the amplitude of the sensed events within a predetermined SRF window T, used in the automatic initialization routine of FIG. 4.

If at 408 an event is sensed, the software resets, at 414, the pacing rate, the pacing mode and the sensitivity threshold to their original or programmed settings. Then, as indicated by block 416, the peak sense and sensitivity threshold are uplinked from the pacemaker 100 to the programmer 200. FIG. 4B is a graph showing the amplitude of the sensed event within the SRF window T. Typically, T is set to about 110 msec. The peak sense is shown in FIG. 4B as 417. The value of the peak sense is digitized and automatically uplinked to the programmer 200. The measured sensitivity threshold 421 is uplinked to the programmer 200. This value is the actual measured value of the programmed threshold. Due to component variation, the programmed threshold may vary from its nominal value by ±20%. As further shown in FIG. 4B, the measured sensitivity threshold 421 is a value below which events are not sensed. A typical value for the programmed threshold is 2.5 millivolts (mV).

Next, the programmer 200 automatically retrieves the value of the safety margin, typically 200%. The safety margin is generally predesignated and preprogrammed to the desired value by each physician. However, the safety margin can be optionally modified by the physician at the onset of the initialization procedure.

The software then automatically calculates the recommended sensitivity threshold value, at 420, using the following equation:

Recommended Sensitivity
Threshold = SRF × Programmed Threshold.

The following example helps to better illustrate the initialization routine 400. If at block 416, the uplinked values of the measured peak sense and measured sensitivity threshold are 12 mV and 3 respectively; and the preprogrammed safety margin is 200 percent; then the SRF factor is:

$$(12\ mv)/\left[(2.75\ mV) \times \frac{(200\% + 100\%)}{100}\right] = 1.45.$$

With a programmed sensitivity threshold of 2.5 mV, the recommended value for the sensitivity threshold becomes: (1.45)×(2.5 mV)=3.63 millivolts. Typically, the calculated sensitivity threshold value would be rounded down to the next most sensitive threshold setting, which, in the above example, is 3.5 mV.

After calculating the recommended value of the sensitivity threshold, the software determines at 422, whether the calculated SRF factor is greater or equal to six. If it is not, as it is illustrated in the above example, then the initialization routine is terminated, and the software returns to block 304. Upon completion of this procedure, the pacemaker is returned to its preprogrammed settings.

If on the other hand, the SRF factor is greater than or equal to 6, then, as indicated at 424, the software temporarily calculates and sets the sensitivity threshold for a SRF factor of 4. The factor of 6 is selected to reflect the dynamic range of the sense amplifier used in the preferred embodiment. However, other values can be assigned to the SRF factor, depending on the type of the sense amplifier used.

A temporarily programmed sensitivity threshold is then calculated:

$$\text{Temporary Sensitivity threshold} = \frac{\text{Peak Sense}}{4 \times \text{Safety Margin}},$$

rounded up to the next highest threshold setting, and temporarily programmed at 424 as noted above.

Thereafter, the software returns to block 406 and repeats the subroutine 406 through 422, with the SRF factor near 4 exiting FIG. 4 to Block 304 via Block 422. Upon completion of this procedure, the pacemaker is returned to its pre-programmed settings.

Turning now to FIG. 5 of the drawings, there is illustrated, in a simplified flow chart format, the automatic initialization routine 500 for selecting the optimal pulse width and amplitude parameters. The object of this initialization routine 500 is to recommend the settings for the pulse amplitude and width which cause minimal current drain on the battery source, and thus leading to an increased longevity of the battery, while simultaneously retaining the desired safety margin.

The software starts the initialization routine 500 at 502, by automatically, temporarily switching the operating mode of the pacemaker 100 to VVI mode. Next, the software determines at 504 whether the programmed lower rate is lower than 100 ppm. If it is, then, as indicated at block 506, the lower rate is temporarily set to 100 ppm, in order to shorten the initialization period, and to ensure a sequence of paced pulses.

If on the other hand, the lower rate is found to be greater than 100 ppm, then, the software leaves the software unchanged. The software then instructs the pacemaker 100 at 508, to continuously uplink peak pressure telemetry values, as valid values, and to turn on the marker channel. The peak pressure values are then uplinked to the programmer 200, at 510, and the software determines at 512, whether the peak pressure is less than 4 millimeters of Mercury (mm Hg).

If it is, then the software discards these values, as indicated at 514. If at block 512 the peak pressure is found to be greater than 4 mm Hg, then the peak value is saved at 520. The software then determines at 518 whether the total count of the valid pressure peaks is equal to 16. If it is not, then the software returns to block 510, and repeats the subroutine until the count is equal to 16.

The software then calculates the average peak pressure over the last sixteen peak pressure value at 522, and the pressure threshold is calculated at 524, as follows:

Recommended Threshold = Average Peak Pressure
Value × Programmed Threshold where the value of the Programmed Threshold may vary from 25–75% and is typically 37½%.

Subsequently, throughout the initialization routine, the software compares the peak pressure value telemetered from the pacemaker to the Recommended threshold. If a peak pressure value is less than the Recommended threshold, capture is determined not to have occurred for that pulse amplitude and pulse width.

Figure 5A:
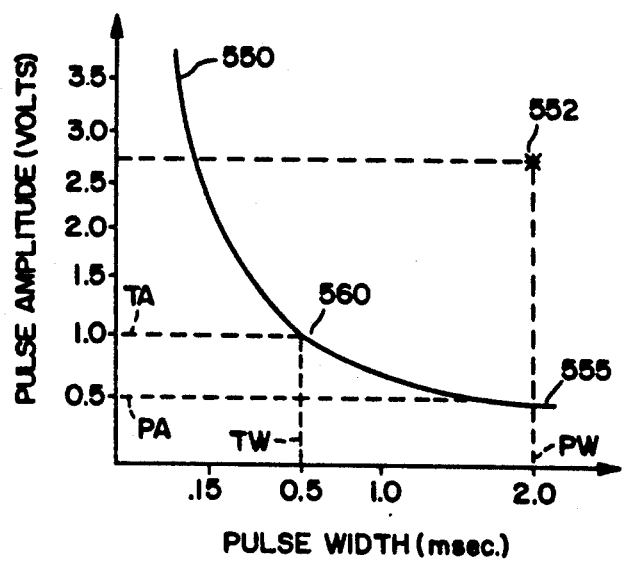
FIG. 5A is a strength duration curve used in the automatic initialization routine of FIG. 5.

The software then determines at 526, whether this is the first test, that is whether the rheobase will be determined. The remainder of the initialization routine 500 will now be described also in relation to FIG. 5A, which illustrates a typical strength duration curve 550. The vertical axis in FIG. 5A represents the pulse amplitude in Volts, and the horizontal axis represents pulse width in milliseconds.

The software then determines at 528 whether this is the initial pulse of this test. If it is, then the software sets the pulse width to 2.0 msec at 530. Let us consider for illustration purposes that the point 552 is the initial setting. Point 552 is located above the strength duration curve 550, and the event is captured. It is the purpose of the present initialization routine to find the rheobase 555, which is defined as the last capture point on the strength duration curve, at a pulse width of 2 msec.

In order to find the rheobase 555, the software decrements the amplitude, as indicated at 532, until capture is lost. Capture is determined by comparing the beat-by-beat value of the peak pulse pressure to the programmed threshold determined at block 524. This is accomplished by the software which inquires at 534 whether capture is lost, and if it has not, then the software repeats the subroutine until capture is lost, and the pulse amplitude (PA) of the rheobase is determined. In the present example, PA is found to be equal to 0.5 volts.

When at 534, it is determined that capture is lost, then the software sets forth to define the chronaxie 560. The chronaxie is defined as the last capture point on the strength duration curve 550 having a pulse amplitude (TA) equal to twice the amplitude (PA) of the rheobase.

For this purpose, the software calculates TA = 2 × PA, as indicated at block 536; then resets amplitude to programmed amplitude to the pacemaker 100 at 538; thereafter sets the following flag: "First Test = False" at 540; and then returns to block 526. Due to this flag, the software then determines at 526 that this is the second test and that it is the chronaxie that should be determined. The software then determines at 541 if this is the initial pulse of the second test. If it is, then the software sets the pulse amplitude to TA (i.e. 1.0 volt in the above example), at 542, and then decrements the pulse width until the chronaxie is located on the strength duration curve 560.

This is accomplished by inquiring at 544, whether capture is lost. If it is not, then the software returns to block 526, and the subroutine is repeated until capture is lost. At which point the software sets the pulse width to TW, that is the pulse width of the chronaxie. In the above example TW = 0.5 msec. The programmed value of pulse width is then reset in the pacemaker 100, at 546.

The programmer then recommends at 547, the following values for the pulse width and amplitude:

Recommended Pulse Width = Pulse Width of the
Chronaxie (PW); and

Recommended Pulse Amplitude = k × the Pulse
Amplitude of the chronaxie (TA), where the "k" coefficient is equal to the square root of the safety margin. The software exits FIG. 5 via block 547 returning to block 308. Upon completion of this procedure, the pacemaker is returned to its pre-programmed settings.

Figure 5B:
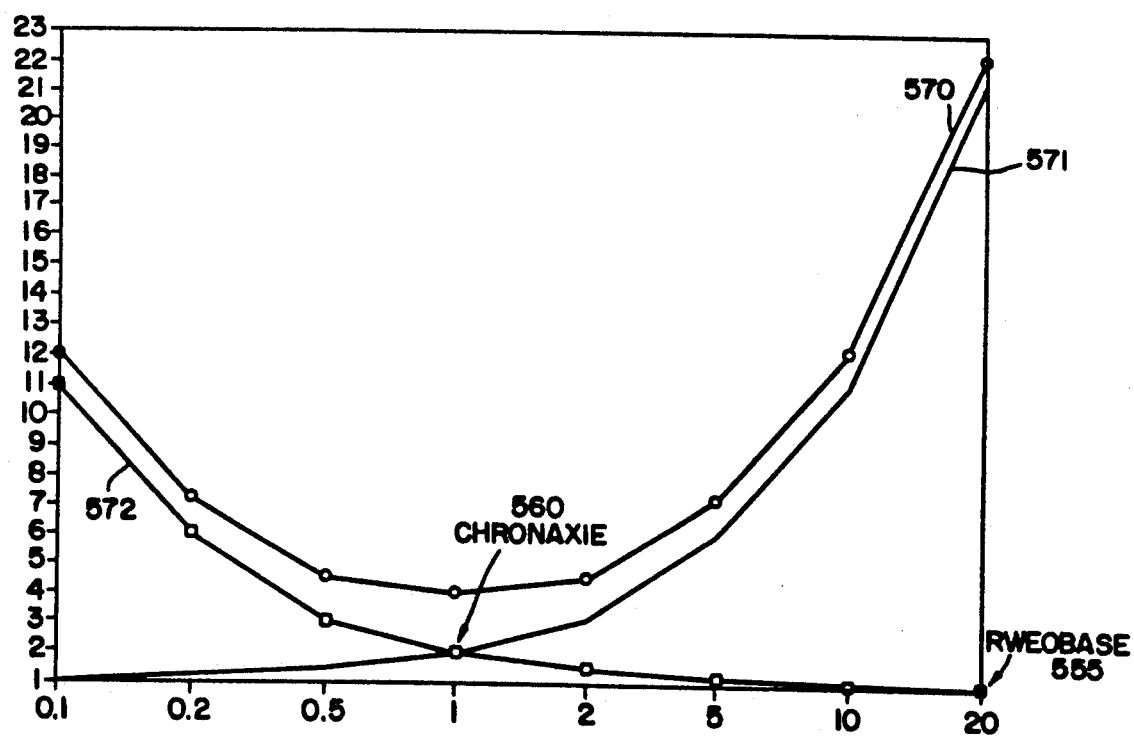
FIG. 5B illustrates three optimized output parameters curves used in the automatic initialization routine of FIG. 5.

The "k" coefficient has been found to be the optimal coefficient, by using the optimized output parameters curves 570, 571 and 572 illustrated in FIG. 5B. The horizontal axis represents the pulse width value normalized to the pulse width at chronaxie. The vertical axis represents the output intensity 572 normalized to the stimulation threshold at rheobase. The charge delivered 571 and energy delivered for stimulation 570 are also shown. As indicated in FIG. 5B, the minimum energy required for stimulation is at the pulse width at chronaxie.

Figure 6:
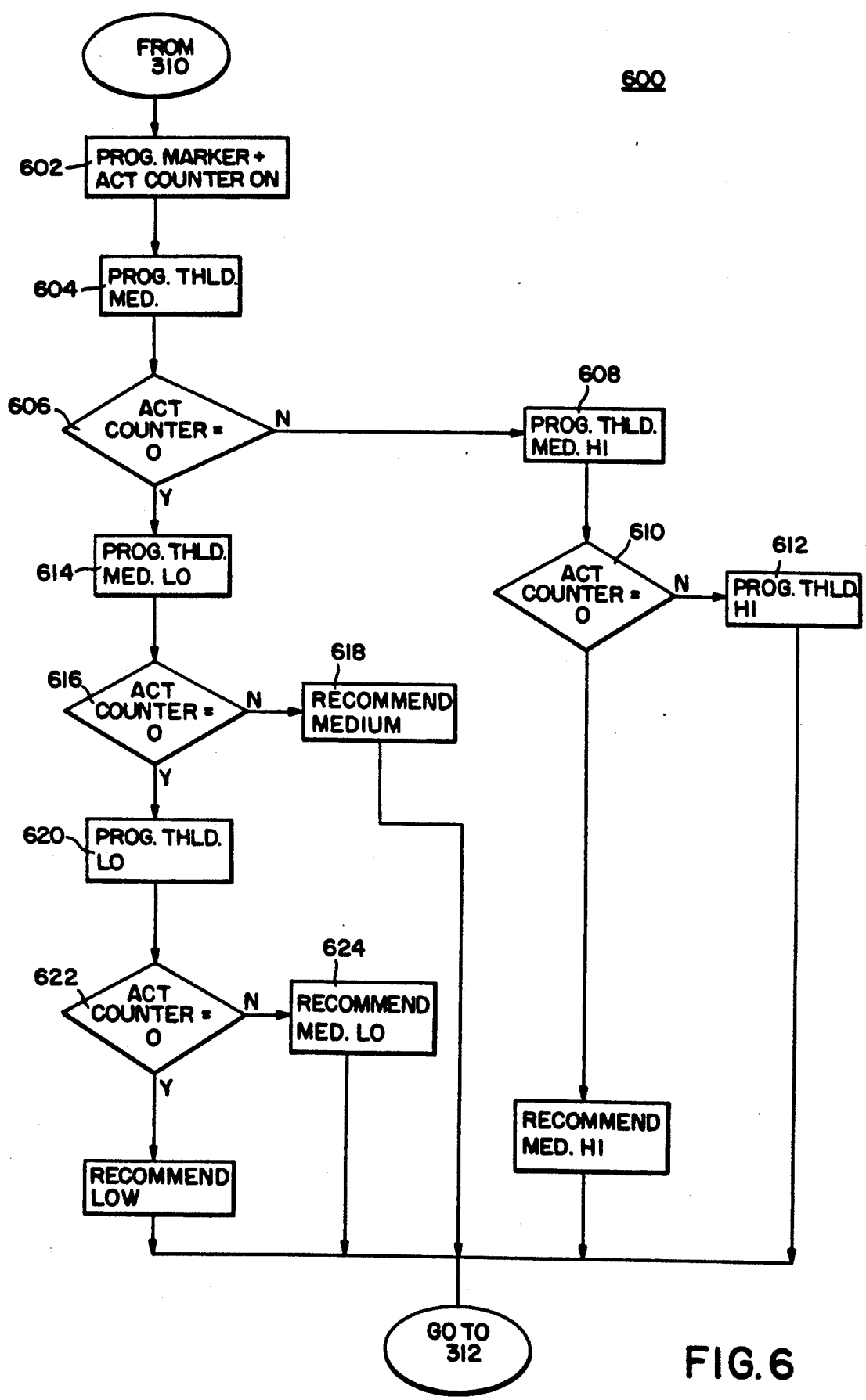
FIG. 6 is a simplified flow chart illustrating an automatic initialization routine for selecting the optimal activity threshold value in accordance with the present invention.

Turning now to FIG. 6, there is illustrated, in a simplified flow chart format, the automatic initialization routine 600 for selecting the optimal activity threshold value. The object of this initialization routine 600 is to recommend the minimum activity threshold setting without getting an activity count, since the patient is in a resting position during the initialization routine 600.

The pacemaker 100 includes 5 settings: LOW, MEDIUM LOW, MEDIUM, MEDIUM HIGH AND HIGH, which correspond to the possible level settings that are make available by the pacemaker 100. The initialization routine 600 automatically recommends the appropriate setting to the physician.

The software starts the initialization routine 600 at 602, by automatically enabling the marker channel as described above, and by setting the activity count telemetry ON. The pacemaker 100 is then set to the MEDIUM activity threshold, as indicated at 604, and the activity counter starts counting the sensed activity events with values uplink via telemetry every 2 seconds.

If at 606 the software determines that the activity count is different than zero, then the activity threshold is automatically programmed to the MEDIUM HIGH setting at 608. If at 610 the counter indicates that the activity count is equal to zero, then the software recommends the MEDIUM HIGH setting and returns to block 312.

If on the other hand the activity count at 610 is not equal to zero, then, as indicated by block 612, the activity threshold is automatically programmed to the HIGH setting, and the software recommends the HIGH setting and returns to block 312.

If at block 606 it is determined that the activity count is equal to zero, then the activity threshold is changed to the MEDIUM LOW setting at 614, and the software inquires once again, at 616, whether the activity count is equal to zero. If it is not, then as indicated at 618, the software recommends the MEDIUM setting as the optimal activity threshold setting, and returns to block 312.

If at 616, the activity count is equal to zero, then the activity threshold is programmed to the LOW setting at 620, and the software inquires once again, at 622, whether the activity count is equal to zero. If it is, then the software recommends the LOW setting as the optimal activity threshold setting, and returns to block 312.

If the software determines at 622 that the activity count is not equal to zero, then the software recommends the MEDIUM LOW setting as the optimal activity threshold setting, and returns to block 312. Upon completion of this procedure, the pacemaker is returned to its pre-programmed settings.

Figure 7A:
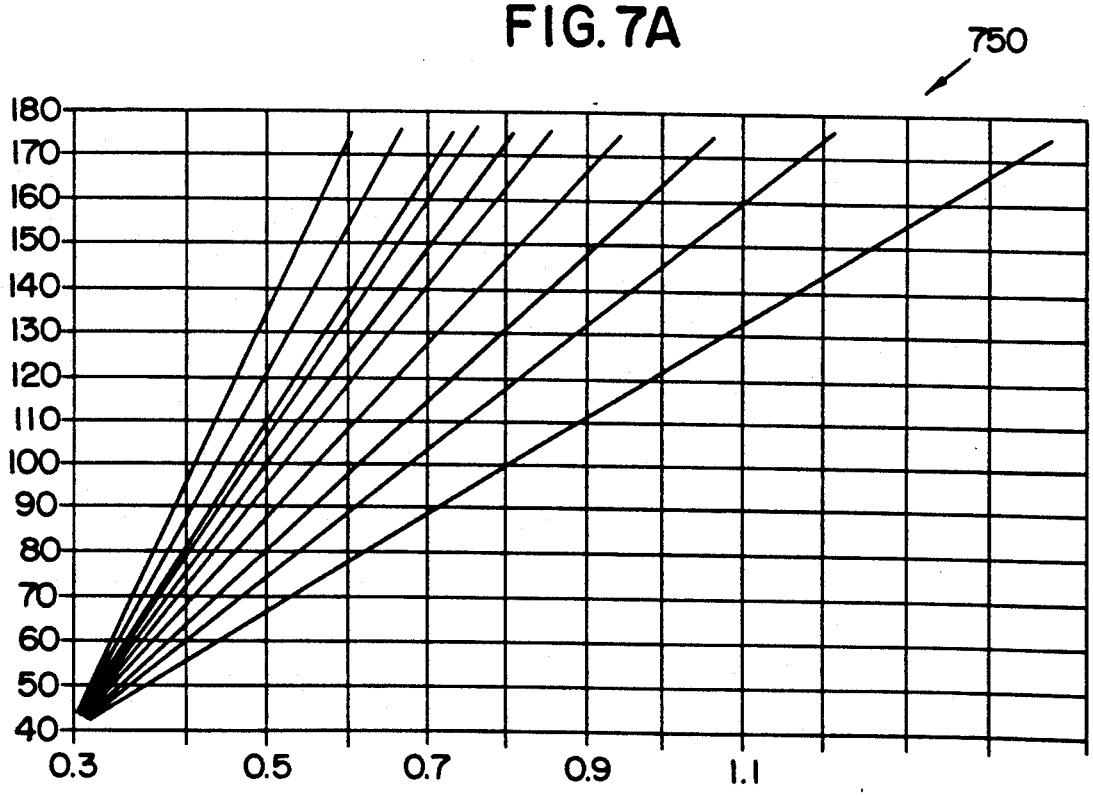
FIG. 7A illustrates a family of ten rate response curves with different gains, for use in the automatic initialization routine of FIG. 7.
Figure 7:
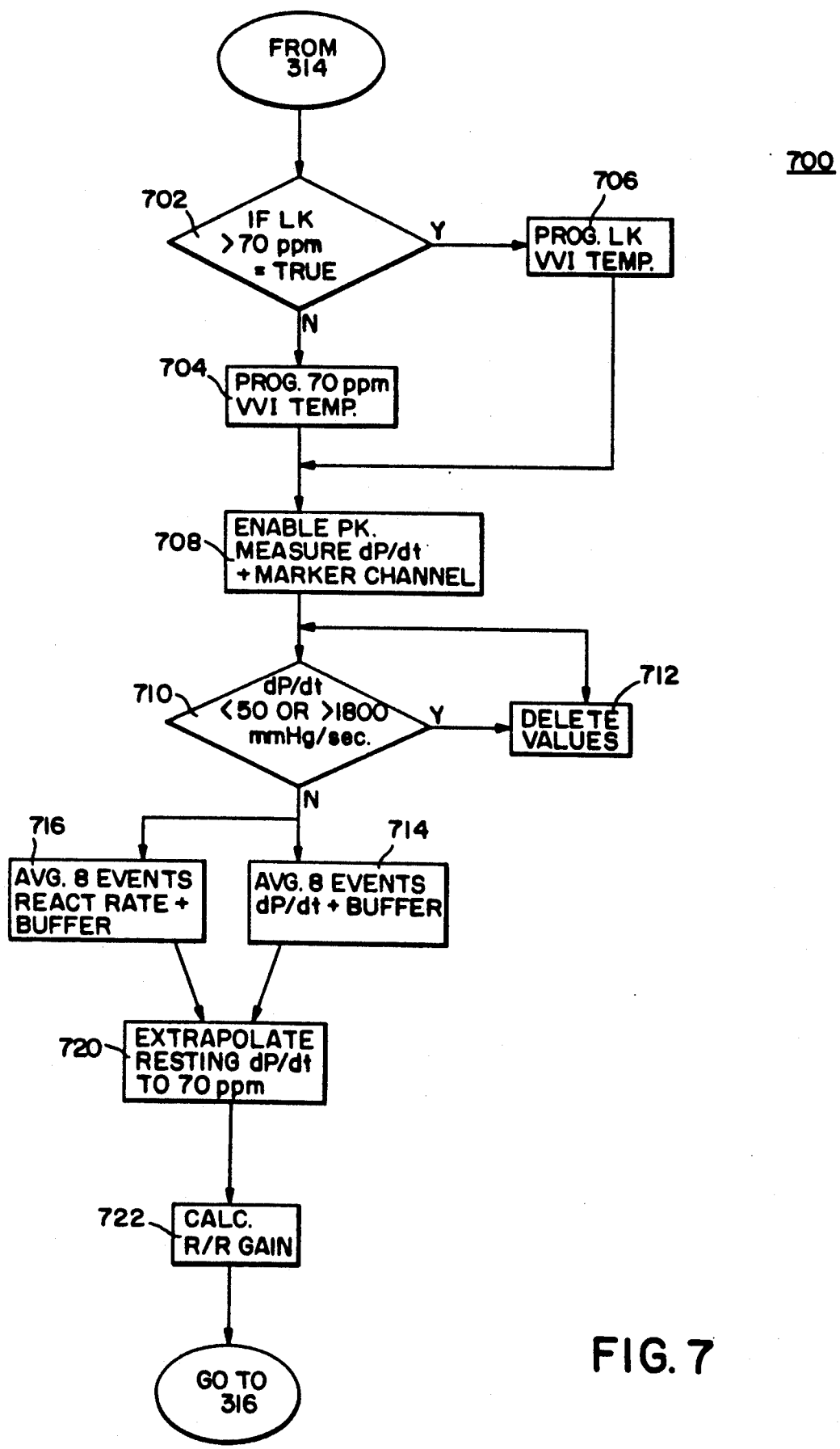
FIG. 7 is a simplified flow chart illustrating an automatic initialization routine for selecting the optimal pressure rate response gain setting, in accordance with the present invention.

Turning now to FIG. 7, there is illustrated, in a simplified flow chart format, the automatic initialization routine 700 for selecting the optimal pressure rate response gain setting. The object of this initialization routine 700 is to recommend a dP/dt rate response gain curve based upon the programmed lower rate/upper rate and an extrapolated resting dP/dt value.

The software starts the initialization routine 700 at 702 by inquiring whether the lower rate is greater than 70 ppm. If it is not, then the software automatically and temporarily sets the pacing rate to 70 ppm, and changes the pacing mode to VVI mode, at 704. If on the hand the lower rate is greater than 70 ppm, then the software changes the pacing mode to VVI mode, at 706, thus leaving the lower rate at its programmed value.

The software then enables the dP/dt peak measurement feature as well as the marker channel, and the pacemaker 100 starts to automatically uplink via telemetry, at 708, the peak dP/dt values of the pressure pulses at the occurrence of each paced or sensed event.

The software then inquires at 710 whether the uplinked dP/dt value ranges between 50 mm Hg/sec and 1800 mm Hg/sec. If it does not, then, as indicated at 712, the measured dP/dt value is rejected as being an artifact, and the software once again makes the same inquiry at 710. If the uplinked dP/dt value ranges between 50 mm Hg/sec and 1800 mm Hg/sec, then this value is saved and the software goes through the same subroutine, until the 8 events are accounted for.

Thereupon, the software simultaneously calculates the average peak dP/dt over the last 8 events, at 714, and the average rate over these same last events, at 716. As defined herein, the resting dP/dt is the arithmetic mean of the peak positive dP/dt measured during a predetermined interval of 8 paced/sensed events with the patient at rest. The resting rate is the arithmetic means of the paced or intrinsic rate over a predetermined interval of 8 paced/sensed events with the patient at rest.

The software then automatically extrapolates the resting dP/dt to 70 ppm, as follows:

$$\text{Resting } dP/dt = [70 \text{ ppm} \times \text{Average Peak } dP/dt]/\text{Average Resting Rate}.$$

Once the extrapolated resting dP/dt value is found, the software sets the 15 rate response gain as follows:

$$\text{Rate Response Gain} = \frac{\text{Upper Rate} - \text{Resting Rate}}{\text{Resting } dP/dt}$$

The software recommends one of the ten rate response curves 750 shown in FIG. 7A, and returns to 316.

Figure 6A:
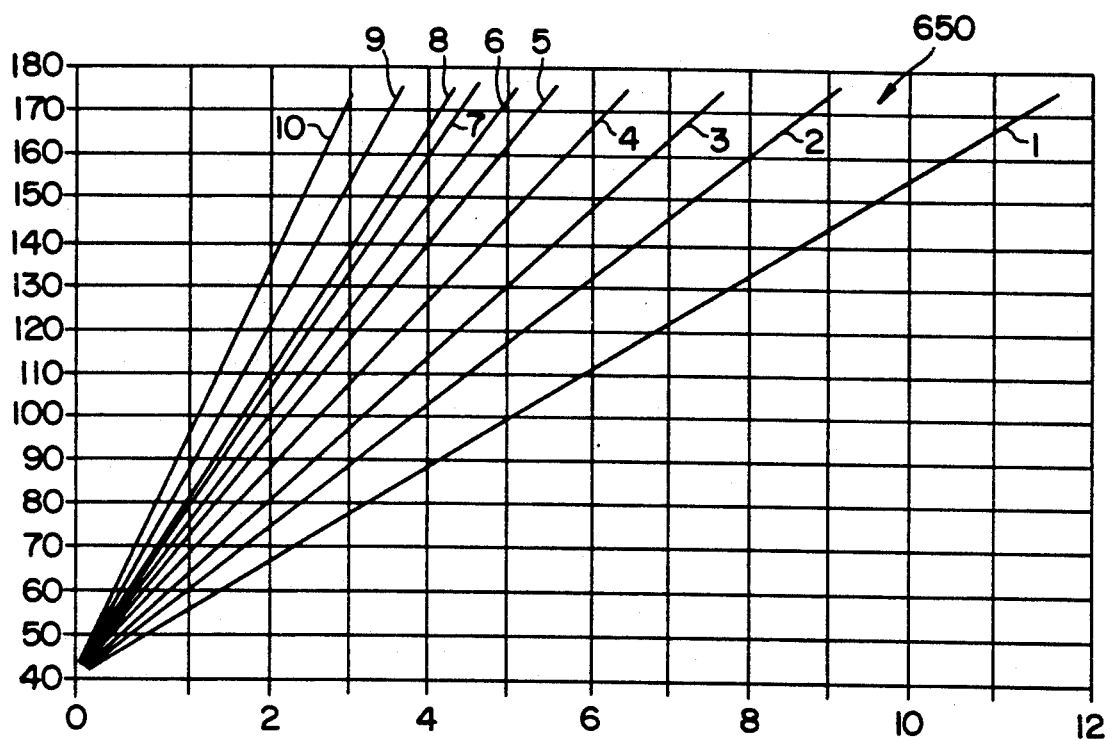
FIG. 6A illustrates a family of ten rate response curves with different gains, for use in the automatic initialization routine of FIG. 6.

FIGS. 6A and 7A graphically illustrate examples of a family of rate response curves for the activity and pressure sensors 102 and 106, respectively. The horizontal axes of each graph correspond to sensor output values being measured. In FIG. 6A, the metric for the horizontal axis corresponds to an activity-based rate control parameter ($RCP_{act}$) and comprises the Activity Count as defined above, which is a function of activity sensor output, expressed in counts per second (Hz). In FIG. 7A, the metric for the horizontal axis corresponds to a pressure-based rate control parameter ($RCP_{press}$) and comprises the dP/dt value determined as defined above, which is a function of pressure sensor output, expressed in mmHg per second. The vertical axes of each graph correspond to a Target Rate, expressed in pulses per minute (ppm).

It can be seen that the Target Rate (TR) for each sensor is thus a function of the respective sensor's output, which functional correlation is defined in more detail below. These Target Rates are utilized by the pacemaker 100 in deriving the rate-responsive pacing rate for the patient's heart.

Ten rate response functions are established for each sensor, such that each function provides for excursion between selected lower and upper pacing rates within the available range of sensor outputs corresponding therewith. Multiple rate response functions are provided to afford the necessary flexibility in providing alternative rate response settings to accommodate for various factors, such as: (a) group-based correlation drift wherein differences exist among a group of patients regarding their respective correlations between the sensor output and corresponding desired pacing rate; (b) individual-based correlation drift wherein the sensor output associated with the rate control parameter being measured does not remain constant over the life of the pacemaker for an individual patient primarily due to physiological changes of the patient over time, such as due to aging; and (c) non-physiological-based correlation drift wherein the sensor output associated with the rate control parameter being measured does not remain constant over the life of the pacemaker sensor primarily due to pacemaker performance changes, such as drift in sensor output.

The various rate response functions shown in FIGS. 6A and 7A are established in conjunction with programmable parameters provided by the patient's physician using an external programmer, in a manner which is generally similar to that described in two co-pending U.S. patent applications, namely, U.S. patent application Ser. No. 455,717, filed on Dec. 22, 1989, entitled "METHOD AND APPARATUS FOR IMPLEMENTING ACTIVITY SENSING IN A PULSE GENERATOR", and U.S. patent application Ser. No. 549,568, filed on Jul. 6, 1990, entitled "PROGRAMMING NON-VOLATILE MEMORY THROUGH HERMETIC FEEDTHROUGH", which are held by the same assignee as the present invention and which are incorporated herein by reference.

The target rates for each rate control parameter are determined as follows:

$$\text{Activity Sensor: } TR_{act} = \frac{(ACTCOUNT + D)}{C} * K$$

$$\text{Pressure Sensor: } TR_{press} = \frac{(PRESSAVG + B)}{A} * K$$

In the above equations, ACTCOUNT and PRESSAVG connote activity count and average dP/dt respectively, the factor $K=(32,768*60/328)$ and is a constant to convert clock cycle, time interval-based data to rate-based data (ppm), and A, B, C, and D constitute variables which are derived from programmed values provided by the external programmer during initialization.

More specifically, variables A, B, C, and D are a function of the programmed Upper Rate (UR), Lower Rate (LR), and the respective rate response gain parameters Activity Gain and Pressure Gain, for specific sensors, or RR in general), and determine the shape desired for the various rate response curves illustrated, for example, in FIGS. 6A and 7A, pacemaker 100 includes an arithmetic logic unit (ALU) capable of generating A, B, C and D values as a function of such programmed parameters, and for making the necessary calculations to generate the respective sensor target rates and controlling the pacemaker rate as a function thereof.

In the rate response graphs of FIGS. 6A and 7A, a range of Target Rates extends between a Resting Rate of 40 ppm and an Upper Rate of 175 ppm. Settings for rate response gain range from 1 to 10. It can be seen, for example, that the same magnitude of change in measured sensor output yields the greatest incremental change in target pacing rate under (10), in contrast to the least incremental change in target pacing rate under (1). The correlation thus defined between the sensor output and target pacing rate under these rate response curves is also often referred to as the "sensor gain function", wherein (10) provides the highest gain and (1) provides the lowest gain.

Each time the physician alters the selected values for UR, LR or RR via telemetry from the external programmer, these updated values are loaded into the program registers of pacemaker 100, such that new A, B, C and D values which are subsequently generated by the pacemaker 100 may be utilized by it in controlling the pacing rate as a function thereof. Regardless of which of selected parameters has changed, the resulting function relating the sensor's Target Rate (TR), will take the basic form, extending from the Lower Rate (LR) at a minimal sensor output to the Upper Rate (UR) at an achievable sensor output, with a sensor output required to achieve UR decreasing as RR is increased.

The programmer 200 also includes means for selection of acceleration and deceleration parameters which limit the rate of change in pacing rate on onset and cessation of activity. Typically, these acceleration and deceleration parameters are referred to in rate-responsive pacemakers as the attack or decay setting, respectively. These may be expressed as the time interval required for the pacemaker to change between the current pacing interval and 90% of the desired pacing interval, assuming that the activity level corresponding to the desired pacing rate remains constant. A more detailed description of the use of the above-described attack/decay settings in conjunction with pacemaker 100, including a modified decay feature which provides a pacing rate which decelerates at more than one decay time constant, is described in co-pending U.S. patent application Ser. No. 567,882, filed on even date herewith, entitled "RATE RESPONSIVE PACEMAKER AND PACING METHOD", which is held by the same assignee as the present invention, and which is incorporated herein by reference.

While particular embodiments of the present invention have been disclosed, it is to be understood that various different modifications are possible and are contemplated within the scope of the specification, drawings, abstract and appended claims.

What is claimed is:

1. A pacemaker system comprising a pacemaker including at least one sense amplifier, said system comprising:
   a. sensor means for sensing pacing parameters; and
   b. means for automatically initializing the sensitivity of said sense amplifiers to an optimized value via automatically optimizing a sensitivity threshold, including processor means for processing the sensed pacing parameters;
   c. said processor means including:
      i) means for periodically determining a sense ratio factor (SRF) according to the following equation:

$$SRF = \frac{(\text{Peak Sense})}{(\text{Sense Threshold}) \times (\text{Recommended Safety Margin})}$$

where Recommended Safety Margin is calculated as follows: Recommended Safety Margin=(% Safety Margin+P %)/100, and Safety Margin and P are programmable values; and ii)

means for determining said optimized sensitivity threshold (Recommended Sensitivity Threshold) by multiplying said SRF by a Programmed Threshold.

2. The pacemaker system as defined in claim 1, further including means for displaying an optimized sensitivity threshold parameter.

3. The pacemaker system as defined in claim 1, wherein a sensitivity threshold pacing parameter is set at an initialized value; and wherein said processor means further includes means for automatically initializing said sensitivity threshold parameter by setting it equal to an optimized sensitivity threshold parameter.

4. The pacemaker system as defined in claim 1, wherein the pacemaker system includes an implantable pacemaker for pacing a human heart, and an external programmer which communicates with said pacemaker and which allows a user to select the pacing parameter to be optimized.

5. The pacemaker system as defined in claim 4, wherein said processor means is at least partially located in said pacemaker.

6. The pacemaker system as defined in claim 4, wherein said processor means is at least partially located in said programmer.

7. A pacemaker system comprising a pacemaker, said system comprising:
   a. pacing pulse generator means for generating pacing pulses; and
   b. means for automatically initializing the pulse width of pacing pulses from said pacing pulse means to an optimized value via automatically establishing a Recommended Pulse Width, said means for automatically initializing including pulse width optimizing means;
   c. said pulse width optimizing means including:
      i) means for measuring peak pressure values;
      ii) means for averaging said peak pressure values over a predetermined interval of time;
      iii) means for determining a rheobase point along a strength duration curve;
      iv) means for determining a chronaxie point based on said rheobase point;
      v) means for determining an initialized pulse width parameter according to the following equation:

Recommended Pulse Width = Pulse Width of the Chronaxie.

8. The pacemaker system as defined in claim 7, further including optimizing means for automatically initializing a pacing pulse amplitude parameter; and wherein said pulse amplitude optimizing means includes means for determining said initialized pulse amplitude parameter according to the following equation:

Pulse Amplitude = k × Pulse Amplitude of Chronaxie, where "k" is a programmable coefficient.

9. The pacemaker system as defined in claim 8, wherein said coefficient "k" is equal to the square root of a recommended safety margin.

10. A pacemaker system comprising an activity-based, rate-responsive pacemaker, said system comprising:
   a. pacing pulse generator means for generating pacing pulses;
   b. rate modulation means coupled to said pacing pulse generator means for modulating said pacing pulses based on sensed activity; and
   c. means for automatically initializing an activity threshold to be used by said rate modulation means to an optimized value including optimizing means;
   c. said optimizing means including:
      i) means for setting the activity threshold to an initial setting;
      ii) means for periodically counting sensed activity events at rest; and
      iii) means for automatically selecting one of a plurality of higher settings for said activity threshold, if said counting means indicates a positive activity count.

11. The pacemaker system as defined in claim 10, wherein said optimizing means further includes means for automatically selecting one of a plurality of lower settings for said activity threshold, if said counting means indicates a zero activity count.

12. A pacemaker system comprising a pacemaker, said system comprising:
   a. pressure rate-response means for changing pacing rates of said pacemaker in response to sensed pressure signals;
   b. sensor means for sending pressure rate response gain threshold signals as sensed pacing parameters to said pressure rate-response means;
   c. processor means for processing the sensed pacing parameters, and for setting optimal values for the pacing parameters;
   d. said processor means including means for automatically optimizing a pressure rate response gain threshold parameter; and
   e. said optimizing means including:
      i) means for counting and measuring valid peak pressure value (dP/dt);
      ii) means for averaging said peak pressure values over a predetermined interval of time;
      iii) means for calculating a resting pressure value according to the following equation:

$$\text{Resting } dP/dt = \frac{[M \times \text{Average Peak } dP/dt]}{\text{Average Resting Rate}},$$

where M is a programmable value in pulses per minute; and
      iv) means for extrapolating said resting pressure value to calculate the rate response gain setting, as follows:

$$\text{Rate Response Gain} = \frac{\text{Upper Rate} - \text{Resting Rate}}{\text{Resting } dP/dt}$$

13. The pacemaker system as defined in claim 12 wherein M is equal to 70 pulses per minute.

14. A pacemaker system comprising a pacemaker, said system comprising:
   a. pacing pulse generator means for generating pacing pulses, said pacing pulse generator means employing a pacing pulse width parameter and a pacing pulse amplitude parameter;
   b. rate modulation means coupled to said pacing pulse generator means for modulating said pacing pulses, said rater modulation means employing an activity threshold parameter and a pressure rate response gain threshold parameter;

c. at least a sense amplifier employing a sensitivity threshold parameter; and d. processor means, said processor means comprising:
   i) first optimizing means for optimizing said sensitivity threshold parameter;
   ii) second optimizing means for automatically initializing said pacing pulse width parameter;
   iii) third means for automatically initializing said pacing pulse amplitude parameter;
   iv) fourth optimizing means for automatically initializing said activity threshold parameter; and
   v) fifth optimizing means for automatically initializing said pressure rate response gain threshold parameter.

* * * * *